US006503947B1

(12) United States Patent
Lipton et al.

(10) Patent No.: US 6,503,947 B1
(45) Date of Patent: Jan. 7, 2003

(54) METHOD OF TREATING CYTOTOXIC DAMAGE

(75) Inventors: Stuart A. Lipton, Newton, MA (US); Dean Le, Cambridge, MA (US); Marcus Kaul, Boston, MA (US); Jonathan S. Stamler, Chapel Hill, NC (US)

(73) Assignee: Brigham and Women's Hospital, Boston, MA (US)

( * ) Notice: Subject to any disclaimer, the term of this patent is extended or adjusted under 35 U.S.C. 154(b) by 0 days.

(21) Appl. No.: 09/239,056

(22) Filed: Jan. 27, 1999

Related U.S. Application Data (60) Provisional application No. 60/072,705, filed on Jan. 27, 1998.

(51) Int. Cl.$^7$ ........................ A61K 31/15; A61K 31/195
(52) U.S. Cl. ........................................ 514/575
(58) Field of Search .......................... 514/575

(56) References Cited

U.S. PATENT DOCUMENTS

| | | | |
|---|---|---|---|
| 5,135,916 A | 8/1992 | Sims et al. | 514/21 |
| 5,243,094 A | 9/1993 | Borg | 568/822 |
| 5,256,642 A | 10/1993 | Fearon et al. | 514/8 |
| 5,472,939 A | 12/1995 | Fearon et al. | 514/8 |
| 5,672,592 A | 9/1997 | Jackson et al. | 514/75 |
| 5,681,721 A | 10/1997 | Steffens et al. | 435/69.6 |
| 5,716,976 A | 2/1998 | Bernstein | 514/386.561 |
| 5,807,671 A | 9/1998 | Soreq et al. | 435/6 |
| 5,824,662 A | 10/1998 | Slusher et al. | 514/75 |
| 5,827,886 A | 10/1998 | Hersh | 514/562 |
| 5,840,896 A | 11/1998 | Van Belle et al. | 544/390 |
| 5,856,300 A | 1/1999 | Rittershaus et al. | 514/12 |
| 5,891,916 A | 4/1999 | Kato et al. | 514/575 |

FOREIGN PATENT DOCUMENTS

| | | |
|---|---|---|
| EP | 07 37671 | 10/1996 |
| WO | WO 94/26786 | 11/1994 |

OTHER PUBLICATIONS

Wolpert et al. Proc. Soc. Exp. Biol. Med., 136(2), 592–6 (1971) (abstract).*
Sahu et al., "Investigation of mechanism–based inhibitors of complement targeting the activated thioester of human C3", Biochemical Pharmacology, 51(6):797–804, 1996.
Choi, Dennis W. "Glutamate Neurotoxicity and Diseases of the Nervous System" Neuron pp. 623–634.
Hacke et al. (1995) "Intravenous Thrombolysis With Recombinant Tissue Plasminogen Activator for Acute Hemispheric Stroke" The Journal of the American Medical Association 274(13): 1017–1025.
Kinouchi et al. (1991) "Attenuation of Focal Cerebral Ischemic Injury in Transgenic Mice Overexpressing CuZn Superoxide Dismutase" Proceedings of the National Academy of Sciences 88(24): 1158–1162.

Lipton et al. (1994) "Excitatory Amino Acids as a Final Common Pathway for Neurologic Disorders" The New England Journal of Medicine 330(9):613–622.
Longa et al. (1989) "Reversible Middle Cerebral Artery Occlusion without Craniectomy in Rats" Stroke 20(1): 84–91.
Meldrum et al. (1990) "Excitatory Amino Acid Neuortoxicity and Neurodegeneratve Disease" Trends in Pharmacological Science Including Toxicological Sciences 11: 379–387.
Memezawa et al. (1992) "Penumbral Tissues Salvages by Reperfusion Following Middle Cerebral Artery Occlusion in Rats" Stroke 23(4): 552–559.
The National Institute of Neurological Disorders and stroke rt–PA Stroke Study Group (1995) "Tissue Plasminogen Activator for Acute Ischemic Stroke" New England Journal of Medicine 8:(24): 1581–1587.
Tsirka et al. (1995) "Excitotoxin–induced Neuronal Degeneration ad Seizure Are Mediated by Tissue Plasminogen Activator" Nature 377(6547):340–344.
Tsirka et al. (1996) "Neuronal Cell Death and tPA" Nature 384(6605): 123–124.
Tsirka et al. (1997) "An Extracellular Proteolytic Cascade Promotes Neuronal Degeneration in the Mouse Hippocampus" The Journal of Neuroscience 17(2): 543–552.
Bederson et al. (1986) "Rat Middle Cerebral Artery Occlusion: Evaluation of the Model and Development of a Neurologic Examination" Stroke 17(3): 472–476.
Buchan et al. (1992) "A New Modle Of Temporary Focal Neurocortical Ischemic In The Rat" Stroke 23(2): 273–279.
Chopp et al. (1994) "Postischemic Administraton Of An Anti–Mac–1 Antibody Reduces Ischemic Cell Damage After Transient Middle Cerebral Artery Occlusion In Rats" Stroke 25(4): 869–876.
Dirnagl et al. (1989) "Continuous Measurement Of Cerebral Cortical Blood Flow By Laser–Doppler Flowmetry In A Rat Stroke Model" Journal Of Cerebral Blood Flow And Metabolism 9(4): 589–596.
Gold et al. (1991) "Animal Models for Arterial Thrombolysis and Prevention of Reocclsion" Supplement to Circulation 83(6): IV26–IV40.
Huang et al. (1994) "Effects of Cerebral Ischemic in Mice Deficient in Neuronal Nitric Oxide Synthase" Science 265(5180): 1883–1885.

(List continued on next page.)

Primary Examiner—Phyllis G. Spivack
(74) Attorney, Agent, or Firm—Fish & Richardson, P.C.

(57) ABSTRACT

The invention features methods of treating cytotoxic damage in a subject comprising administering to the subject a substance which is a complement inhibitor, free radical scavenger, or both, to thereby treat cytotoxic damage. The methods of the invention can be used to treat cytotoxic damage associated with a non-thrombotic or thrombotic condition. Methods of treating thrombotic conditions such as stroke and/or ischemia in a subject, comprise administering a thrombolytic agent and a substance which is a complement inhibitor, free radical scavenger or both.

55 Claims, 5 Drawing Sheets

OTHER PUBLICATIONS

Lin et al. (1993) "Effect of Brain Edema on Infarct volume in a Focal Cerebral Ischemia Model in Rats" *Stroke* 24(1): 117–121.

Makrides, Savvas C. (1998) "Therapeutic Inhibition of the Complement System" *Pharmacological Review* 50(1): 59–87.

Rosenburg et al. (1996) "Proteolytic Cascade Enzymes Increase in Focal Cerebral Ischemia in Rat" *Journal of Cerebral Blood Flow and Metabolism* 16(3): 360–366.

Sappino et al. (1993) "Extracellular proteolysis in the adult murine brain" *The Journal of Clinical Investigation* 92(2): 679–685.

Soriano et al. (1996) "Intercellular Adhesion Molecule–1–deficient Mice are Less Susceptible to Cerebral Ischemia–Reperfusion Injury" *Annals of Neurology* 39(4): 618–624.

Swanson et al. (1990) "A Semiautomated Method for Measuring Brain Infarct Volume" *Journal of Cerebral Blood Flow and Metabolism* 10(2): 290–293.

Tsirka et al. (1997) "Neuronal Death In The Central Nervous System Demonstrates A Non–Fibrin Substrate For Plasmin" *Proceedings Of The National Academy Of Sciences Of The United States Of America* 94(18): 9779–9781.

Yang et al. (1994) "Human Copper–Zinc Superoxide Dismutase Tansgenic Mice Are Highly Resistant To Reperfusion Injury After Focal Cerebral Ischemia" *Stroke* 25(1): 165–170.

Yang et al. (1994) "Reperfusion–induced injury to the blood–brain barrier after middle cerebral artery occlusion in rats" *Stroke* 25(8): 1658–1665.

Yasuda et al. (1991) "Kistrin, A Polypeptide Platelet Gpiib/Iiia Receptor Antagonist, Enhances And Sustains Coronary Arterial Thrombolysis With Recombinant Tissue–Type Plasminogen Activator In A Canine Preparation" *Circulation* 83(3): 1038–1047.

Zhang et al. (1994) "Anti–ICAM–1 Antibody Reduces Ischemic Cell Damage After Transient Middle Cerebral Artery Occlusion In The Rat" *Neurology* 44(9): 1747–1751.

Zhang et al. (1994) "Nitric Oxide Increase Blood Flow and Reduce Brain Damage in Focal Ischemia: Evidence that Nitric Oxide is Beneficial in the Early States of Cerebral Ischemia" *Journal of Cerebral Blood Flow and Metabolism* 14(2) 217–226.

Zhang et al. (1994) "Reduction of Focal Cerebral Ischemic Damage by Delayed Treatment with Nitric Oxide Donors" *Journal of Cerebral Blood Flow and Metabolisms* 14(4): 574–580.

Kamii et al. (1994) "Prolonged Expression Of Hsp70 mRNA Following Transient Focal Cerebral Ischemia In Transgenic Mice Overexpressing CuZn–Superoxide Dismutase" *Journal of Cerebral Blood Flow and Metabolisms* 14(3): 478–486.

Bednar et al. (1997) "Activation Of Complement By Tissue Plasminogen Activator, But Not Acute Cerebral Ischemia, In A Rabbit Model Of Thromboembolic Stroke" *Journal Of Neurosurgery* 86(1): 139–142.

Belayev et al. (1995) "Hu–211, a Novel Noncompetitive N–Methyl–D–Aspartate Antagonist, Improves Neurological Deficit and Reduces Infarct Volume After Reversible Focal Cerebral Ischemia in Rat" 26(12): 2513–2320.

Bennett et al. (1987) "Activation Of The Complement System By Recombinants Tissue Plasminogen Activator" *Journal Of The American College Of Cardiology* 10(3): 627–631.

Connolly et al. (1996) "Procedural and Strain–related Variable Significantly Affect Outcome in a Murine Model of Focal Cerebral Ischemia" *Neurosurgery* 38(3): 523–532.

Garcia et al. (1995) "Neurological Deficit and Extent of Neuronal Necrosis Attributable to Middle cerebral Artery Occlusion in Rats" *Stroke* 26(4): 627–635.

Taparelli, C. (1993) "Synthetic Low–Mlecular Weight Thrombin Inhibitors: Molecular Design and Pharmacological Profile" *Trends in Pharmacological Sciences* 14(10): 366–376.

Tsirka (1997) "Clinical Implications of the Involvement of tPA in Neuronal Cell Death" *Journal of Molecular Medicine* 75:341–347.

* cited by examiner

METHOD OF TREATING CYTOTOXIC DAMAGE

This application claims benefit of provisional application 60/072,705 filed Jan. 27, 1998.

INTRODUCTION

Stroke is the third most common cause of death in the United States. Intravenous injection of the serine protease tissue plasminogen activator (tPA) has been approved by the U.S. Food and Drug Administration as the first agent that combats focal cerebral infarction or stroke. Studies have shown that tPA administered as a thrombolytic agent within 3 hours of the insult can dissolve the blood clot(s) responsible for initiating cerebral damage (rt-PA Stroke Study Group, N.Engl. J. Med. 333, 1581–1587 (1995) and Hacke et aL JAMA 274, 1017–1025 (1995)). However, the use of tPA in acute ischemic stroke is reported to carry substantial risk of intracerebral hemorrhage.

SUMMARY

The present invention is based, at least in part, on the discovery that complement activation and free radical formation contribute to cytotoxic damage associated with stroke and other neurological disorders. In addition, it was found that fibrinolytic agents such as tPA, which can be used as a thrombolytic agent, contribute to cytotoxic damage associated with stroke and other neurological disorders. Accordingly, in one aspect, the invention features a method of treating cytotoxic damage associated with non-thrombotic conditions in a subject. The method includes administering to the subject a substance which is complement inhibitor, a free radical scavenger, or both, to thereby ameliorate cytotoxic damage associated with non-thrombotic conditions in the subject. In a preferred embodiment the subject is a mammal, e.g., a human.

In a preferred embodiment, the non-thrombotic condition is a neurodegenerative disease, e.g., Huntington's disease, AIDS dementia complex, neuropathic pain syndromes, Olivopontocerebellar atrophy, Parkinsonism, amyotrophic lateral sclerosis, mitochondrial abnormalities, MELAS syndrome, Leber's disease, Wernicke's encephalopathy, Rett syndrome, homocysteinuria, hyperhomocysteinemia, hyperprolinemia, nonketotic hyperglicinemia, hydroxybutyric aminoaciduria, sulfite oxidase deficiency, combined systems disease, lead encephalopathy, Alzheimer's disease, hepatic encephalopathy, and Tourette's syndrome. In another preferred embodiment, the non-thrombotic condition is an acute neurologic disorder, e.g., hypoglycemia, hypoxia, anoxia, poisoning by carbon monoxide, poisoning by manganese, poisoning by cyanide, mechanical trauma to the brain, mechanical trauma to the spinal cord, and epilepsy. In another preferred embodiment, the subject is suffering from: a convulsive disorder; neuropathic pain; glaucoma. In another preferred embodiment, a non-thrombotic condition includes a drug related condition, e.g., a condition associated with drug addiction, drug dependence, drug withdrawal, or drug tolerance.

In a preferred embodiment, the invention comprises identifying an individual at risk for cytotoxic damage associated with a non-thrombotic condition. In a preferred embodiment, the individual is at risk for cytotoxic damage associated with: a neurodegenerative disease; an acute neurologic disorder; a drug related condition; a convulsive disorder; neuropathic pain; glaucoma.

In a preferred embodiment, the substance is a complement inhibitor such as a soluble complement re mptor type 1 protein. In another preferred embodiment, the substance is a complement inhibitor, a free radical scavenger, or both, which can cross the blood-brain barrier, e.g., the substance is a hydroxamic acid derivative, e.g., salicylhydroxamic acid (SHA) or acetohydroxamic acid (AHA); a substituted amide; a substituted hydroxylamine; an aldoxime, e.g., salicylaldoxime; a hydroxyphenyl compound, e.g., catechin or a derivative thereof or hydrocaffic acid or a derivative thereof; a terpene; oleanolic acid; or an ephedra. In a preferred embodiment, the substance is a complement inhibitor, a free radical scavenger, or both, which has a molecular weight of 600 or less.

In a preferred embodiment, the substance is a complement inhibitor, a free radical scavenger, or both which is administered in a pharmaceutically acceptable formulation. In a preferred embodiment, the substance which is a complement inhibitor, a free radical scavenger or both is administered intraperitoneally, orally, intravascularly, subcutaneously, intradermally, intramuscularly, intranasally, intracerebral-ventricularly (ICV), or intratracheally.

In a preferred embodiment, the substance which is a complement inhibitor, a free radical scavenger, or both is administered at a level of approximately 40–4,000 mg/Kg, 200–2000 mg/Kg or 400–1,000 mg/Kg.

In a preferred embodiment, the cytotoxic damage is mediated through glutamate receptors.

In another aspect, the invention features a method of treating cytotoxic damage in a subject. The method includes administering to the subject a substance which is a complement inhibitor, a free radical scavenger, or both, wherein the substance is able to cross the blood-brain barrier and thereby treat cytotoxic damage in the subject, e.g., a mammal, e.g., a human. In a preferred embodiment, the method further includes administering a thrombolytic agent to the subject. In a preferred embodiment, the thrombolytic agent is a fibrinolytic agent, e.g. a plasminogen activator (e.g., a tissue plaminogen activator (t-PA) or Desmodus salivary plasminogen activator (dsPA)), a streptokinase, and/or a urokinase. The thrombolytic agents can be produced recombinantly.

In a preferred embodiment, the subject includes a subject suffering from stroke, ischemia, e.g., cerebral ischemia, focal cerebral ischemia, global cerebral ischemia, and hypoxia ischemia. In a preferred embodiment, the invention comprises identifying an individual at risk for a cytotoxic damage associated with stroke. In the preferred embodiment, the individual is at risk of developing cytotoxic damage associated with one or more of the following: stroke, ischemia, e.g., cerebral ischemia, focal cerebral ischemia, global cerebral ischemia, and hypoxia ischemia.

In a preferred embodiment, the subject suffers from a neurodegenerative disease, e.g., Huntington's disease, AIDS dementia complex, neuropathic pain syndromes, Olivopontocerebellar atrophy, Parkinsonism, amyotrophic lateral sclerosis, mitochondrial abnormalities, MELAS syndrome, Leber's disease, Wernicke's encephalopathy, Rett syndrome, homocysteinuria, hyperhomocysteinemia, hyperprolinemia, nonketotic hyperglicinemia, hydroxybutyric aminoaciduria, sulfite oxidase deficiency, combined systems disease, lead encephalopathy, Alzheimer's disease, hepatic encephalopathy, and Tourette's syndrome. In another preferred embodiment, the subject is suffering from an acute neurologic disorder, e.g., hypoglycemia, hypoxia, anoxia, poisoning by carbon monoxide, poisoning by manganese, poisoning by cyanide, mechanical trauma to the brain, mechanical trauma to the spinal cord, and epilepsy. In another preferred embodiment, the subject is suffering from:

a convulsive disorder; neuropathic pain; glaucoma; or a drug related condition, e.g., a condition associated with drug addiction, drug dependence, drug withdrawal, and drug tolerance.

In the preferred embodiment, the individual is at risk of developing cytotoxic damage associated with: a neurodegenerative disorder; an acute neurologic disorder; a convulsive disorder; a drug-related condition; neuropathic pain; glaucoma.

In a preferred embodiment, the substance is a complement inhibitor, e.g., a soluble complement receptor type 1 protein. In another preferred embodiment, the substance is a complement inhibitor, a free radical scavenger, or both, which can cross the blood-brain barrier, e.g., the complement inhibitor, free radical scavenger, or both is a hydroxamic acid derivative, e.g., salicylhydroxamic acid (SHA) or acetohydroxamic acid (AHA); a substituted amide; a substituted hydroxylamine; an aldoxime, e.g., salicylaldoxime; a hydroxyphenyl compound, e.g., catechin or a derivative thereof, or hydrocaffic acid or a derivative thereof; a terpene; oleanolic acid; or an ephedra. In a preferred embodiment, the substance is a complement inhibitor, a free radical scavenger, or both which has a molecular weight of 600 or less.

In a preferred embodiment, the substance which is a complement inhibitor, a free radical scavenger, or both is administered in a pharmaceutically acceptable formulation. In a preferred embodiment, the substance is administered intraperitoneally, orally, intravascularly, subcutaneously, intradermally, intramuscularly, intranasally, intracerebralventricularly (ICV), or intratracheally.

In another preferred embodiment, the substance is a complement inhibitor, a free radical scavenger, or both which is administered at a level of approximately 40–4,000 mg/Kg, 200–2,000 mg/Kg or 400–1,000 mg/Kg.

In a preferred embodiment of the invention, the cytotoxic damage is mediated through glutamate receptors.

In another aspect, the invention features a method of treating plasminogen activator induced cytotoxic damage in a subject suffering from stroke. The method comprises administering to the subject a substance which is a complement inhibitor, a free radical scavenger, or both, wherein the substance is able to cross the blood-brain barrier to thereby treat plasminogen activator induced cytotoxic damage in the subject.

In a preferred embodiment, the plasminogen activator induced cytotoxic damage is tissue-plasminogen activator (tPA) induced cytotoxic damage or Desmodus salivary plasminogen activator (dsPA) induced cytotoxic damage.

In a preferred embodiment, the invention comprises identifying an individual at risk for plasminogen activator induced cytotoxic damage associated with stroke, e.g., tPA or dsPA induced cytotoxic damage.

In another aspect, the invention features a method of treating plasminogen activator induced cytotoxic damage in a subject suffering from cerebral ischemia. The method includes administering to the subject a substance which is a complement inhibitor, a free radical scavenger, or both, wherein the substance is able to cross the blood-brain barrier to thereby treating plasminogen activator induced cytotoxic damage in the subject.

In a preferred embodiment, the plasminogen activator induced cytotoxic damage is tissue-plasminogen activator (tPA) induced cytotoxic damage or Desmodus salivary plasminogen activator (dsPA) induced cytotoxic damage.

In a preferred embodiment, the invention comprises identifying an individual at risk for plasminogen activator induced cytotoxic damage associated with cerebral ischemia, e.g., tPA or dsPA induced cytotoxic damage. In the preferred embodiment, the individual at risk of developing plasminogen activator induced cytotoxic damage, e.g., tPA or dsPA induced cytotoxic damage, is associated with one or more of the following: cerebral ischemia; focal cerebral ischemia; global cerebral ischemia; and hypoxia ischemia.

In another aspect, the invention features a method of treating cytotoxic damage in a subject. The method comprises administering to the subject a hydroxamic acid derivative to thereby treat cytotoxic damage in the subject. In a preferred embodiment, the hydroxamic acid derivative is salicylhydroxamic acid (SHA) or acetohydroxamic acid (AHA).

In a preferred embodiment, the subject includes a subject suffering from stroke, ischemia, e.g., cerebral ischemia, focal cerebral ischemia, global cerebral ischemia, and hypoxia ischemia. In a preferred embodiment, the invention comprises identifying an individual at risk for a cytotoxic damage associated with stroke. In the preferred embodiment, the individual is at risk of developing cytotoxic damage associated with one or more of the following: stroke, ischemia, e.g., cerebral ischemia, focal cerebral ischemia, global cerebral ischemia, and hypoxia ischemia.

In a preferred embodiment, the subject suffers from a neurodegenerative disease, e.g., Huntington's disease, AIDS dementia complex, neuropathic pain syndromes, Olivopontocerebellar atrophy, Parkinsonism, amyotrophic lateral sclerosis, mitochondrial abnormalities, MELAS syndrome, Leber's disease, Wernicke's encephalopathy, Rett syndrome, homocysteinuria, hyperhomocysteinemia, hyperprolinemia, nonketotic hyperglicinemia, hydroxybutyric aminoaciduria, sulfite oxidase deficiency, combined systems disease, lead encephalopathy, Alzheimer's disease, hepatic encephalopathy, and Tourette's syndrome. In another preferred embodiment, the subject is suffering from an acute neurologic disorder, e.g., hypoglycemia, hypoxia, anoxia, poisoning by carbon monoxide, poisoning by manganese, poisoning by cyanide, mechanical trauma to the brain, mechanical trauma to the spinal cord, and epilepsy. In another preferred embodiment, the subject is suffering from: a convulsive disorder; neuropathic pain; glaucoma; or a drug related condition, e.g., a condition associated with drug addiction, drug dependence, drug withdrawal, and drug tolerance.

In the preferred embodiment, the individual is at risk of developing cytotoxic damage associated with: a neurodegenerative disorder; an acute neurologic disorder; a convulsive disorder; a drug-related condition; neuropathic pain; glaucoma.

In another aspect, the invention features a pharmaceutical preparation comprising an anti-thrombolytic agent and at least one substance which is a complement inhibitor, a free radical scavenger, or both, wherein the substance is able to cross the blood-brain barrier. In a preferred embodiment, the substance is: hydroxamic acid derivatives; substituted amides; substituted hydroxylamines or aldoximes; hydroxyphenyl compounds; terpenes; or ephedra. In a preferred embodiment, the anti-thrombolytic agent is a plasminogen activator (e.g., tissue plasminogen activator (t-PA) or Desmodus salivary plasminogen activator (dsPA)).

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

DETAILED DESCRIPTION

The invention is based, at least in part, on the discovery that complement activation and free radical formation contribute to cytotoxic damage associated with stroke and other neurological disorders. Such cytotoxic damage can result in cellular dysfunction, deterioration and/or cell death. Thus, administration of a substance which is a complement inhibitor, a free radical scavenger, or both can be used to treat, inhibit or prevent cytotoxic damage.

The complement system is a host defense mechanism against infection and plays an important role in the inflammatory response. There are at least 25 complement proteins, which are found as a complex collection of plasma proteins and membrane cofactors. Complement components achieve their immune defense functions by interacting through three enzymatic pathways (classical, lectin and alternative pathways). Activation of any one of these complement pathway eventually leads to formation of the membrane attack complex (MAC) containing C5b-9 which binds to a target cell, creates pores in the cell membrane thereby causing cell lysis. A detailed description of both the classical and alternative pathways can be found, for example, in Low and Reed, Complement, 2nd ed., IRL Press, Oxford University Press, New York, N.Y., 1995.

Complement Inhibitors

A substance which is a complement inhibitor can be any molecule which inhibits or reduces activation of complement, e.g., of the classical, lectin and/or alternative pathway. For example, a complement inhibitor can include any molecule that can inhibit or reduce, directly or indirectly, the initiation of the complement cascade, the transcription of a complement gene, the expression of a complement component (e.g., a complement protein or co-factor), the activity of a complement component or cofactor (e.g., complement factors C1–C9, e.g., C3) so as to reduce complement activity. A complement inhibitor can be a naturally occurring molecule (e.g., an endogenous complement regulatory protein, e.g., C1 inhibitor), a modified derivative of a naturally occurring molecule (e.g., soluble complement receptor 1), or a non-naturally occurring molecule (e.g., a chemical compound), or a drug.

Various endogenous complement inhibitors can be used. Endogenous complement inhibitors are well known in the art. For example, C3 endogenous inhibitor proteins include decay accelerating factor (DAF). DAF inhibits or reduces complement activity by accelerating the decay of C3A and/or C5A convertase and inhibits amplification of the complement cascade on host cell membranes. Membrane cofactor protein (MCP), Factor H, C4b-binding protein and complement receptor 1 (CR1 or CD35) inhibit or reduce complement by triggering the degradation of C3 and C5 convertases and/or membrane bound C3b molecules. Other endogenous inhibitors affecting other members of the complement cascade are also known. For example, C5b-9 inhibitor proteins include human glycoprotein CD59; C5b-7 inhibitor, e.g., vitronectin; and, C1 inhibitor protein, e.g., the C1 inhibitor. Isolated native complement inhibitor proteins and recombinant forms of endogenous complement inhibitors are available commercially.

Modified naturally occurring complement components can also be used as a complement inhibitor. For example, several modified derivatives of naturally occurring molecules can be used to inhibit complement activation. Such complement inhibitors include soluble complement receptor type 1, soluble complement-receptor type 1 lacking long homologous Repeat-A, and soluble DAF. Examples of such complement inhibitors are described, for example, in Makrides, S. C. *Pharmacological Reviews* 50:59–78 (1998), the contents of which is incorporated herein by reference.

Microbial pathogens are also known to produce complement inhibitor proteins. Such pathogens include *Entamoeba histolyica, Tryansoma cruzi,* and *Salmonella choleraesuis.* Additionally, viruses are also known to inhibit the complement cascade, e.g., Herpesvirus Saimiri expresses a C3 complement protein referred to as CCPH and vaccinia virus expresses a VCP protein.

Other proteins known to inhibit the complement cascade can be used, such as cobra venom and antibodies reactive with the complement components. For example, monoclonal antibodies against C5b-9 are described in U.S. Pat. No. 5,135,916 the contents of which are incorporated herein by reference.

In addition, complement inhibitors include complement inhibitor proteins that are recombinantly expressed, e.g., immunoglobulins and single chain antibodies.

A complement inhibitor can also include synthetic chemical compounds. Such compounds include 3,3'-ureylenebis [6-(2-amino-8-hydroxy-6-sulfp-1-naphthylazo) benzenesulfonic acid, tetrasodium salt, Suramin sodium, tranexamic acid and heparin. Of particular interest are complement inhibitors that can cross the blood brain barrier. Such complement inhibitors include hydroxamic acid derivative (e.g., salicylhydroxamic acid (SHA) or acetohydroxamic acid (AHA)); a substituted amide; a substituted hydroxylamine; an aldoxime (e.g., salicylaldoxime); a hydroxyphenyl compound (e.g., catechin or hydrocaffic acid); a terpene; oleanolic acid; and an ephedra. Complement inhibitors are available commercially from, for example, from Parke-Davis, Anarbor, Mich. and Behringer AG, Morburg, Germany.

A substance which is complement inhibitor can also be a free radical scavenger. The term "free radical scavenger", as used herein, refers to agents reactive with oxygen free radicals or nitrogen free radicals, e.g., nitric oxide. Examples of such free radical scavengers include hydroxamic acid derivatives (e.g., salicylhydroxamic acid (SHA) and acetohydroxamic acid (AHA)).

Other substances which are complement inhibitors, free radical scavengers or both can be tested for their ability to prevent cytotoxic damage using, for example, the middle cerebral artery (MCA) occlusion stroke model as described in Longa et al., *Stroke* 20, 84–91 (1989). Briefly, mice are anthesthized with isoflurane and maintained at a constant temperature of 36+1° C. A 6.0 monofilament nylon suture with silicone-coated tip is then advanced about 9 mm into the internal carotid artery via the external carotid artery. Immediately after the filament is secured, a candidate substance (e.g., complement inhibitor, free radical scavenger or both), or control (normal saline) can be injected. One and a half-hours after the first injection, a second injection can be given to the animal. A half hour following the second injection, the animals are re-anesthetized and the filament can be removed to allow reperfusion. Cerebral blood flow, blood pressure, blood gases, pH, and serum glucose are monitored. After 24 hours, the animals can be sacrificed, the brain removed and sliced into sections, e.g., cut on a vibratome. The brain slices can then be stained with 2% triphenyltetrazolium choloride. The ability of a candidate substance to reduce and/or prevent cytotoxic damage can be assessed by determining the infarct volume as described in Swanson et al., *J. Cereb. Blood Flow Metab.* 10, 290–293 (1990).

The substances described herein to treat cytotoxic damage are not limited to just one mechanism of action, and thus, may function as a complement inhibitor, a free radical scavenger, as both, or by other mechanisms.

Anti-thrombotic Agents

An anti-thrombotic agent, as used herein, refers to an agent that inhibits or reduces blood clot formation (e.g., inhibits or reduces thrombosis) and/or stimulates thrombolysis (i.e., thrombus dissolution). Various agents, including aspirin, protaglandin E1, selective thromoxane A2 inhibitors, selective thrombin inhibitors, platlelet receptor GPIIb/IIIa blockers, streptokinase, heparin, complement inhibitors and kistrin can be used as an anti-thrombotic agent, see Yasuda et al., (*Circulation* 83:1028 (1991) and Gold et al., *Circulation* (Supplement IV) 83:IV26 (1991). In addition, anti-thrombotic agents for use can include fibrinolytic agents, e.g., serine proteases, e.g., plasminogen activators, e.g., tissue plasminogen activator (tPA) and/or Desmodus salivary plasminogen activator (dsPA). Anti-thrombotic agents are available commercially. For example, tPA is commercially available from Genentech, San Francisco, Calif., and dsPA is commercially available from Burlex.

The present invention features administering a substance which is a complement inhibitor, a free radical scavenger, or both, and optionally when treating certain disorders, e.g., focal stroke, administering simultaneously or sequentially an anti-thrombotic agent to dissolve the offending blood clot. The administration of the substance which is a complement inhibitor, a free radical scavenger or both, with an anti-thrombotic agent can reduce the cytotoxic effects of the anti-thrombotic agent. Any anti-thrombotic agent can be administered with the substance.

Cytotoxic Damage

The substance which is a complement inhibitor, a free radical scavenger, or both, can be administered to a subject, e.g., a human, to treat cytotoxic damage. The terms "treat" and "treatment", as used herein, refer to the reduction, inhibition or prevention of at least one symptom associated with cytotoxic damage. Cytotoxic damage, as used herein, refers to physical deterioration, dysfunction (e.g., abnormal growth and/or reproduction) and/or death of a cell, e.g., nerve cell. Such damage can be the result of disease, injury and/or aging. For example, cytotoxic damage can arise due to under or over production of a substance or substances by nerve cells (e.g., a neurotransmitter, or a metabolic substance, e.g., superoxide ion, nitric oxide, other free radical species or lactic acid), overstimulation of a cell receptor (e.g., a nerve cell receptor, e.g., a glutamate receptor, e.g., a ionotropic or metabotropic receptor), failure of nerve cells to produce a substance or substances which it normally produces (e.g., neurotransmitter), failure of cell transporter system (e.g., uptake transporter, e.g., an ion channel), failure of and/or transmission of electrical impulses in abnormal patterns or at abnormal times, exposure of a cell to excessive amounts of a molecule (e.g., the exposure of neurons to glutamate, e.g., by release of glutamate from neuronal vesicular stores), and the deprivation of a substance to a cell (e.g., oxygen or glucose). In addition, cytotoxic damage can arise in a cell following exposure of a cell to a toxin or a poisonous molecule. For example, cells can be exposed to a toxic or a poisonous molecule by ingestion or inhalation. The molecule can be a naturally occurring molecule (e.g., lead, manganese, cyanide) or can be a protein that is endogenously expressed in the cell (e.g., tPA). Alternatively, the molecule can be a non-naturally occurring molecule, e.g., a chemical or a drug, e.g., trimetrexate or S-fhorourcil. The toxin or poisonous molecule can cause injury or death to a cell, e.g., by directly or indirectly initiating the apoptotic or programmed cell death pathway, or by interfering with normal physiological processes, e.g., inhibiting electron transport. In addition, cytotoxic damage can occur due to mechanical trauma (e.g., physical injury caused by violent or disruptive action) or can occur in response to exposure to a gas (e.g., carbon monoxide).

Of particular interest is cytotoxic damage occurring, at least in part, due to overstimulation of a nerve cell receptor, e.g., a glutamate receptor, e.g., a ionotropic or a metabotropic receptor. Overstimulation of a glutamate nerve cell receptor can result in the excessive influx of calcium into a neuron. Excessive amount of calcium may contribute to overstimulation of normal processes, causing damage or death to the nerve cell. Many known neurologic disorders are mediated, at least in part, through glutamate receptors. These disorders include but are not limited to neurodegenerative disease, acute neurologic disorders, convulsive disorders, neuropathic pain and glaucoma. Examples of neurodegenerative disorders that are mediated, in part, through glutamate receptors include Huntington's disease, AIDS dementia complex, neuropathic pain syndromes, Olivopontocerebellar atrophy, Parkinsonism, amyotrophic lateral sclerosis, mitochondrial abnormalities, MELAS syndrome, Leber's disease, Wernicke's encephalopathy, Rett syndrome, homocysteinuria, hyperhomocysteinemia, hyperprolinemia, nonketotic hyperglicinemia, hydroxybutyric aminoaciduria, sulfite oxidase deficiency, combined systems disease, lead encephalopathy, Alzheimer's disease, hepatic encephalopathy, Tourette's syndrome, drug addiction, tolerance and dependency. Examples of acute neurologic disorders also thought to be mediated through stimulation of glutamate receptors include hypoglycemia, hypoxia, anoxia, poisoning by carbon monoxide, poisoning by manganese, poisoning by cyanide, mechanical trauma to the brain, mechanical trauma to the spinal cord, stroke (cerebral ischemia or hypoxia-ischemia) and epilepsy. Individuals with such pathological conditions in need of the presently claimed treatment may be identified by methods known to medical practitioners trained in the relevant areas of medical practice.

Other factors such as tPA or dsPA can also contribute to nerve cell death. For example, tPA can contribute to cytotoxic nerve cell damage or death by activating the complement system or increasing free radical formation. Activation of either the classical or alternative complement pathways by tPA can contribute to death of neuronal cells thereby causing the release of intracellular stores of glutamate from nerve cells. The release of glutamate from a cell can, in turn, cause the overactivation of glutamate receptors in adjacent nerve cells. The present invention provides a method for inhibiting, treating or preventing cytotoxic damage by administering a substance which is a complement inhibitor, free radical scavenger, or both and/or an inhibitor of a plasminogen activator (e.g., tPA and/or dsPA), e.g., serine protease inhibitors, e.g., protease nexin-1 and/or C1 inhibitor.

Cytotoxic damage associated with non-thrombotic conditions include any condition that is not directly caused by a blood clot. For example, stroke can be either occlusive (i.e., due to closure of a blood vessel) or hemorrhagic (i.e., due to bleeding from a vessel). Cytotoxic damage caused by thrombosis or an embolism is a considered to be a thrombotic condition. One skilled in the art would be able to determine whether cytotoxic damage is associated with a non-thrombotic condition or a thrombotic condition.

Administration of Complement Inhibitors

A substance which is a complement inhibitor, a free radical scavenger, or both is administered to a subject, e.g., a human, to thereby ameriolate or inhibit cytotoxic damage. As used herein, the term subject refers to a mammal. Examples of mammals include human and non-human primates (e.g., a monkey), goats, pig, cow, and rodent (e.g., a rat or mouse) having a disorder associated with cytotoxic damage. The mammal is preferably a primate, e.g., a human. The term "administering", as used herein, refers to delivery of a substance which is a complement inhibitor, a free radical scavenger, or both, alone or in combination with one or more compounds, e.g., an anti-thrombotic agent. When administered with other therapeutic agents, e.g., anti-thrombotic agents, the substance can be administered simultaneously or sequentially with the other agent. For example, in stroke patients, an anti-thrombotic agent such as tPA or dsPA can be administered after a complement inhibitor. When administered simultaneously, the substance which is a complement inhibitor, a free radical scavenger, or both can be administered as part of a pharmaceutical preparation which also comprises another agent, e.g., an anti-thrombotic agent, e.g., tPA or dsPA.

Administration of a substance which is a complement inhibitor, a free radical scavenger, or both can include local or systemic administration. Examples of suitable routes of administration include intraperitoneal, oral, intravenous, subcutaneous, intradermal, intramuscular, intracerebralventricularly (ICV) and intratracheal administration. Various methods can be used to administer the therapeutic complement inhibitor, free radical scavenger, or both directly to a specific site in the body, e.g., X-ray imaging can be used to assist in certain of the above delivery methods.

Receptor-mediated targeted delivery of therapeutic compositions containing complement inhibitor polynucleotides can be used to deliver a complement inhibitor. Receptor-mediated DNA delivery techniques are known in the art and described, for example, in Findeis et al. (1993), *Trends in Biotechnol.* 11, 202–05; Chiou et al. (1994), GENE THERAPEUTICS: METHODS AND APPLICATIONS OF DIRECT GENE TRANSFER (J. A. Wolff, ed.); Wu & Wu (1988), *J. Biol. Chem.* 263, 621–24; Wu et al. (1994), *J. Biol. Chem.* 269, 542–46; Zenke et al. (1990), *Proc. Natl. Acad. Sci. U.S.A.* 87, 3655–59; Wu et al. (1991), *J. Biol. Chem.* 266, 338–42.

Alternatively, a complement inhibitor can be introduced into human cells ex vivo, and the cells then replaced into the subject, e.g., human. Cells can be removed from a variety of locations including, for example, from a selected neural tissue or from an affected organ.

The substance which is a complement inhibitor, a free radical scavenger, or both can also be incorporated into a pharmaceutical composition suitable for administration. Such compositions typically comprise a substance which is a complement inhibitor, a free radical scavenger, or both and a pharmaceutically acceptable carrier. As used herein, the term "pharmaceutically acceptable carrier" is intended to include all solvents, dispersion media, coatings, antibacterial and antifungal agents, isotonic and absorption delaying agents, and the like, compatible with pharmaceutical administration. The use of such media and agents for pharmaceutically active substances is well known in the art. Such carriers include, but are not limited to, large, slowly metabolized macromolecules, such as proteins, polysaccharides, polylactic acids, polyglycolic acids, polymeric amino acids, amino acid copolymers, and inactive virus particles. Pharmaceutically acceptable salts can also be used in the composition, for example, mineral salts such as hydrochlorides, hydrobromides, phosphates, or sulfates, as well as the salts of organic acids such as acetates, proprionates, malonates, or benzoates. The composition can also contain liquids, such as water, saline, glycerol, and ethanol, as well as substances such as wetting agents, emulsifying agents, or pH buffering agents. Liposomes, such as those described in U.S. Pat. No. 5,422,120, WO 95/13796, WO 91/14445, or EP 524,968 B1, can also be used as a carrier.

Typically, a composition comprising a therapeutic complement inhibitor, free radical scavenger, or both is prepared as an injectable, either as a liquid solution or suspension. However, solid forms suitable for solution in, or suspension in, liquid vehicles prior to injection can also be prepared. The composition can also be formulated into an enteric coated tablet or gel capsule according to known methods in the art, such as those described in U.S. Pat. No. 4,853,230; European Patent No. 225,189 and Australian Patent No. 9,224,296.

The substance which is a complement inhibitor, a free radical scavenger, or both is administered to the subject in a therapeutically effective amount. A "therapeutically effective amount" refers to an amount which is capable of, at least partially, reducing, alleviating or preventing cytotoxic damage. A therapeutically effective amount can be determined on an individual basis and is based, at least in part, on consideration of the species of mammal, the mammal's size, the agent used, the type of delivery system used, the time of administration relative to the severity of the disease, and whether a single, multiple, or a controlled release dose regimen is employed. A therapeutically effective amount can be determined by one of ordinary skill in the art employing such factors and using no more than routine experimentation.

Effective dosages of a substance which is a complement inhibitor, free radical scavenger, or both include the range of about 40 mg/kg to about 4000 mg/kg of patient body weight, about 200 mg/kg to about 2000 mg/kg, and about 400 mg/kg to about 1000 mg/kg of patient body weight. For gene therapy protocols, a therapeutic composition comprising a complement inhibitor can be administered in a range of about 100 ng to about 200 mg of DNA for local administration. Concentration ranges of about 500 ng to about 50 mg, about 1 µg to about 2 mg, about 5 µg to about 500 µg, and about 20 µg to about 100 µg of DNA can also be used during a gene therapy protocol. Factors such as method of action and efficacy of transformation and expression are considerations that will effect the dosage required for ultimate expression of the complement inhibitor. Where greater expression is desired over a larger area of tissue, larger amounts of complement polynucleotides or the same amounts readministered in a successive protocol of administrations, or several administrations to different adjacent or close tissue portions may be required to effect a positive therapeutic outcome. In all cases, routine experimentation in clinical trials will determine specific ranges for optimal therapeutic effect.

EXAMPLES

Cerebral Infarcts tPA-deficient and Wild-type Mice

Figure 1:
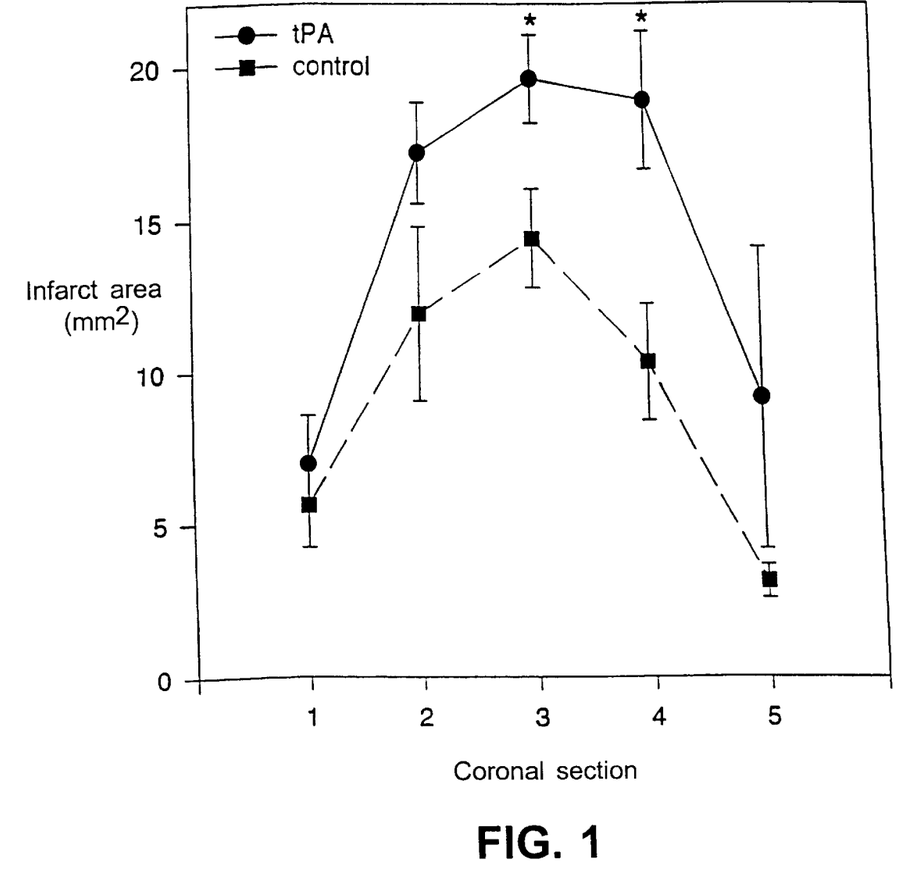
FIG. 1 is a line graph depicting the infarct area for each of the 5 coronal sections of brains from saline-injected or tPA-injected tPA deficient mice undergoing a 3-hour occlusion of the middle cerebral artery (MCA) followed by 21 hours of (mean+s.e.m.).
Figure 2:
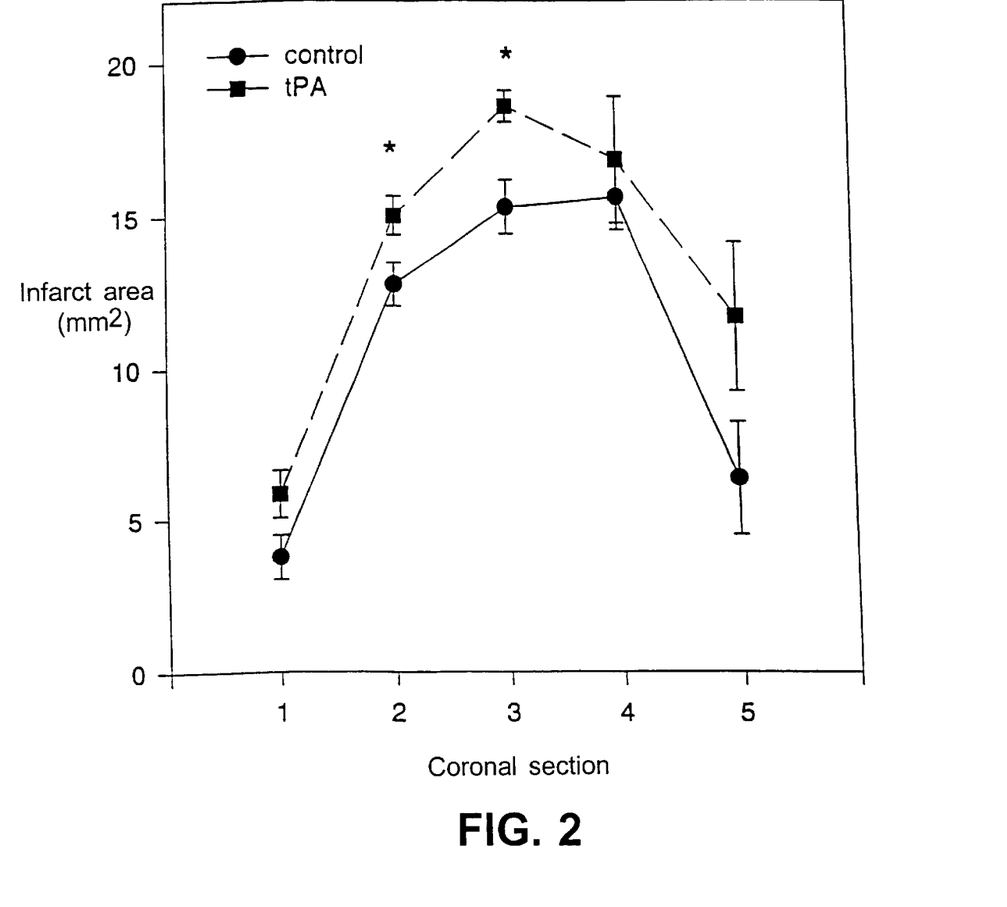
FIG. 2 is a line graph depicting the infarct area for each of the 5 coronal sections of the brains from (BSA)-injected or tPA-injected (0.9 mg/kg) wild-type (C57BL/6) mice undergoing a 2 hour vascular occlusion followed by 22 hours of reperfusion (mean±s.e.m., $P<0.05$).
Figure 3:
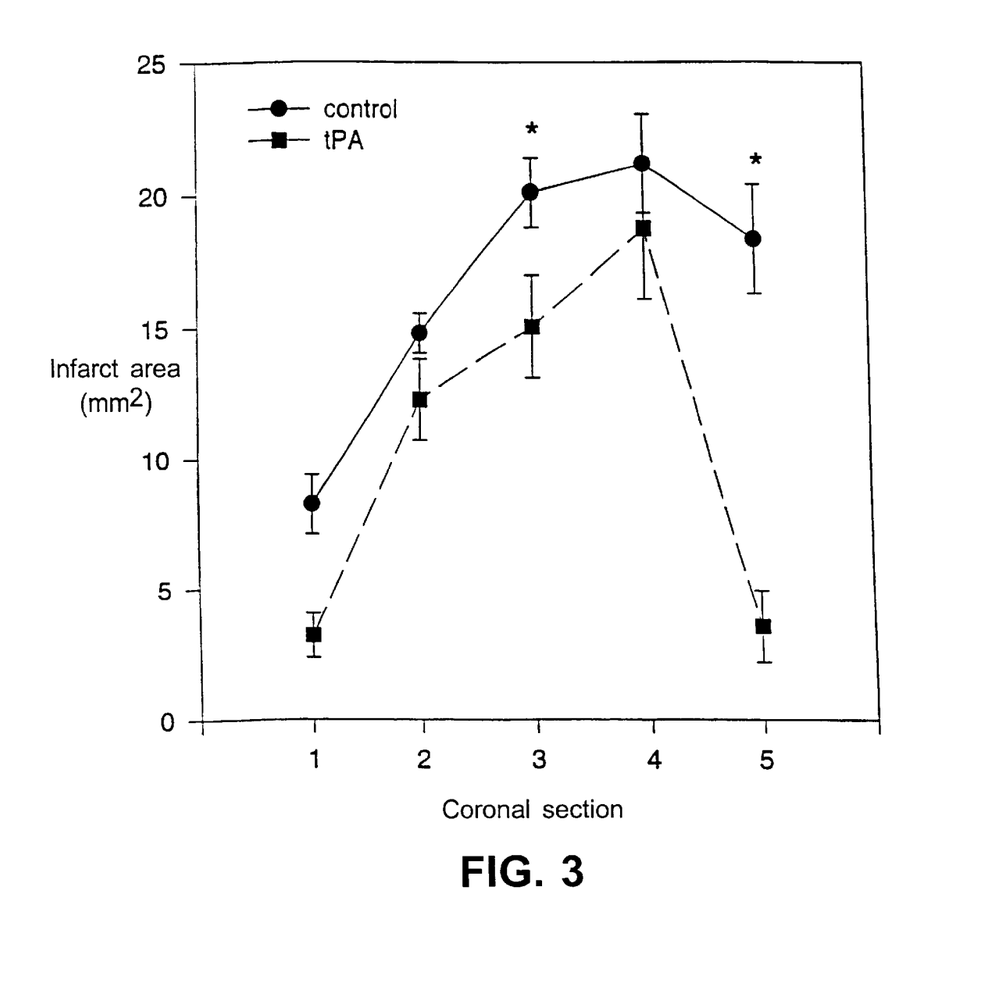
FIG. 3 is a line graph depicting the infarct area for each of the 5 coronal sections of the same brains of control solution (Genentech tPA diluent)-injected or tPA-injected (0.9 mg/kg) wild-type (SV 129) mice undergoing a 2 hour vascular occlusion followed by 22 hours of reperfusion (mean±s.e.m., $P<0.003$).

Wild-type and tPA-deficient male mice (on C57Black/6 and SV129 backgrounds) weighing 23–27 grams were housed in a 12 hour light/dark cycle and permitted food and water intake ad libitum. Transient ischemia/reperfusion was performed using the intravascular filament model to occlude the middle cerebral artery unilaterally for 2 or 3 hours followed by reperfusion for the remainder of the 24 hour period as described in Longa et al., *Stroke* 20, 84–91 (1989) and Soriano. et al. *Ann. Neurol.* 39, 618–624 (1996). Briefly, under isoflurane anesthesia, a 6.0 nylon filament coated with silicone was threaded into the lumen of the middle cerebral artery of mice (C57Black/6 and SVI29 backgrounds) to produce transient ischemia. After 2 or 3 hours of occlusion, the filament was gently withdrawn to allow tissue reperfusion. Body temperature was maintained at 36.5±1.0° C. Systemic arterial blood pressure was monitored via a femoral arterial line until 30 minutes after all surgical interventions and did not vary among the various groups. Other physiological parameters including arterial blood gases and glucose also did not vary significantly among the groups. Animals were sacrificed 24 hours after the onset of the insult as described in Huang et al. *Science* 265, 1883–1885 (1994) and Soriano, supra. Infarct volumes were digitally quantified on 1.5 mm thick coronal sections after correction for edema by measuring TTC staining, as described in Soriano, supra, Bederson et al., *Stroke* 17,472–476 (1986); Swanson et al., *J. Cereb. Blood Flow Metab.* 10, 290–293 (1990), Lin et al., *Stroke* 24, 117–121 (1993); Zhang, et al., *Neurology* 44, 1747–1751 (1994); and Chopp et al. *Stroke* 25, 869–876 (1994)). Infarct volume decreased from 116±8 mm$^3$ in control wild-type mice to 69±7 mm$^3$ in tPA-deficient mice (mean±s.e.m., n=19 mice), as shown in FIG. 1. Under these conditions, there is no thrombosis at the occluded site, so the absence of tPA would not contribute to damage via an enhanced clotting cascade. Hence, this technique allowed for the distinction between effects of tPA as a thrombolytic from effects on neurotoxicity.

Parallel to the ischemia damage occurring unilaterally on the side of the vascular occlusion in the wild-type mice, a significant increase in tPA activity was observed, most likely due to the accumulation of microglial cells at the site of the injury. Activated microglia are known to secrete tPA (Tsirka et al., *J. Neurosci.* 17, 543–552 (1997)). Following ischemic injury/reperfusion, the status of microglial cells in the tPA-deficient mice was evaluated using immunohistochemistry against the mature macrophage/microglial cell surface antigen F4/80. Wild-type mice were subjected to 2 hours of focal ischemia per 10 minute reperfusion. After this the animals were sacrificed, their brains frozen and sectioned (12 gm). Microglia were visualized by immunohistochemistry with an antibody to the mature macrophage/monocyte antigen F4/80 (Serotec, Raleigh, N.C.), as described previously Tsirka et al., *Nature* 377, 340–344 (1995). It was observed that microglia were activated in the wild-type mice but activation was attenuated in tPA-/-mice.

Intravenous Injection of tPA into tPA-deficient or Wild Type Mice

To determine the effect of intravenous injection of tPA into tPA-deficient or wild-type mice (C57BL/6 or SV129), intravenous tPA was administered intravenously, 10% initially by bolus, followed by constant infusion over twenty to thirty minutes at 0.9–1.0 mg/kg (similar to rt-PA Stroke Study Group, *N. Engl J. Med.* 333, 1581–1587 (1995) and Hacke. et al. *JAMA* 274, 1017–1025 (1995). The formula for the carrier used to dilute tPA was obtained from the manufacturer (Genentech, San Francisco, Calif.) and was used as one of the control injections. The diluent consisted of 0.02 M arginine phosphate at pH 7.3 with 0.001% Tween. It was found that tPA dramatically increased the size of cerebral infarction when occlusion was due to the intraluminal filament, causing a near doubling of the damage in tPA-deficient mice and approximately a 20–35% increase in wild-type mice. No hemorrhage or other bleeding diathesis occurred in any of the animals, as analyzed at postmortem examination. In wildtype, but not tPA deficient mice, ischemia induced an increase in tPA activity, as assessed by histological zymography. Briefly, wild-type or tPA deficient mice were subjected to 2 hours of focal ischemia. After 10 minutes of reperfusion, the animals were sacrificed and their brains frozen as described previously (Tsirka et al., *Nature* 377, 340–344 (1995)). Then, 12 µm consecutive coronal brain cryostat sections were subjected to histological zymography to visualize tPA activity with or without amiloride (1 mM, a specific urokinase [uPA] inhibitor) (Sappino et al *J. Clin. Invest.* 92, 679–685 (1993) and Rosenberg et al., *Cereb. Blood Flow Metab.* 16, 360–366 (1996)). The sections were overlaid with a milk-agarose substrate matrix containing 50 ug/ml of purified human plasminogen and 1 mg/ml amiloride. Photographs were taken under dark field illumination after a 3 hour incubation at 37° C. The tPA-deficient mice were also useful in demonstrating that intravenous administration of exogenous tPA resulted in the apparent entry of tPA activity into the brain. Taken together, these data reinforce that toxic actions of tPA may, under these conditions, adversely affect cerebral damage. Of note, however, in the face of large cerebral infarcts in wildtype mice (e.g., induced by 3 rather than 2 hours of vascular occlusion), injection of tPA did not enhance the size of the stroke over control animals not receiving tPA, suggesting a ceiling effect. This result is consistent with the finding that large infarcts activate a high level of endogenous tPA activity in the area of the insult.

Effect of tPA on Neuronal Viability

To assess the possibility that an adverse effect of tPA during cerebral ischemia influenced neuronal viability, neuronal loss was quantified in the hippocampus. Quantification of neuronal loss in the CA1–CA3 hippocampal subfields was performed as described in Tsirka et al., *J. Neurosci.* 17, 543–552 (1997). Briefly, wild-type or tPA deficient mice were subjected to 3 hours of ischemia/21 hours reperfusion as detailed above. The mice were then sacrificed, the brains removed and quickly frozen in cold acetone in a dry iceethanol bath. Serial cryostat sections 12 pm in thickness were cut and stained with cresyl violet. Four consecutive sections from the dorsal hippocampus of mice from each genotype were visually matched. The hippocampal subfields (CA1–CA3) in each of these sections were traced from camera lucida. The length of each subfield was then measured by comparison to 1 mm standards traced under the same magnification. In each subfield, the length of tissue was scored with viable pyramidal neurons (having normal morphology) and length of tissue with neuronal loss (no cresyl violet staining and no cells present). The lengths representing intact neurons and neuronal loss for each hippocampal subfield were averaged across all sections and standard deviations calculated. A dramatic difference in the number of surviving neurons was observed in the CA1–CA3 subfields following 3 hours of ischemia and 21 hours of reperfusion in the wild-type versus tPA deficient brains. Neuronal loss was much more marked in wild-type compared to tPA-1- mice (74±9% neuronal loss in WT compared to 10±3% in tPA-deficient mice; mean±s.d., n=6 brains, P<0.001). Similarly, more extensive neuronal cell death was also evident in the cerebral cortex of wild-type compared to tPA deficient mice.

Evaluation of Cerebral Blood Flow

Regional cerebral blood flow was also monitored by the laser Doppler flowmetry technique as described in Dimagl et al *J. Cereb. Blood Flow Metab.* 9, 589–596 (1989); Zhang et al., *J. Cereb. Blood Flow Metab.* 14, 217–226 (1994); and Zhang et al., *J. Cereb. Blood Flow Metab.* 14, 574–580 (1994) to insure that there were no differences between control and tPA-deficient mice, either before, during or after the induction of ischemia. Briefly, the initial reading of regional Cerebral Blood Flow (rCBF) was assigned a value of 100% and subsequent readings were expressed relative to this value. Flow was monitored in the ischemic core as judged by the fact that the rCBF fell to virtually 0% during occlusion of the middle cerebral artery. rCBF was measured by laser Doppler flowmeter (Vasamedics BPM, Minneapolis, Minn.), using methods previously described in Soriano et al., supra. A probe tip was fixed approximately 6 mm lateral and 2 mm posterior to the bregma in the anesthetized animals. This site corresponds to the distal arterial supply of the middle cerebral artery. We found that with reperfusion the cerebral blood flow was partially restored to levels that were not significantly different between the wild-type, tPA-deficient, or tPA-injected mice for each group of experiments.

Pharmacokinetics of SHA

Figure 4:
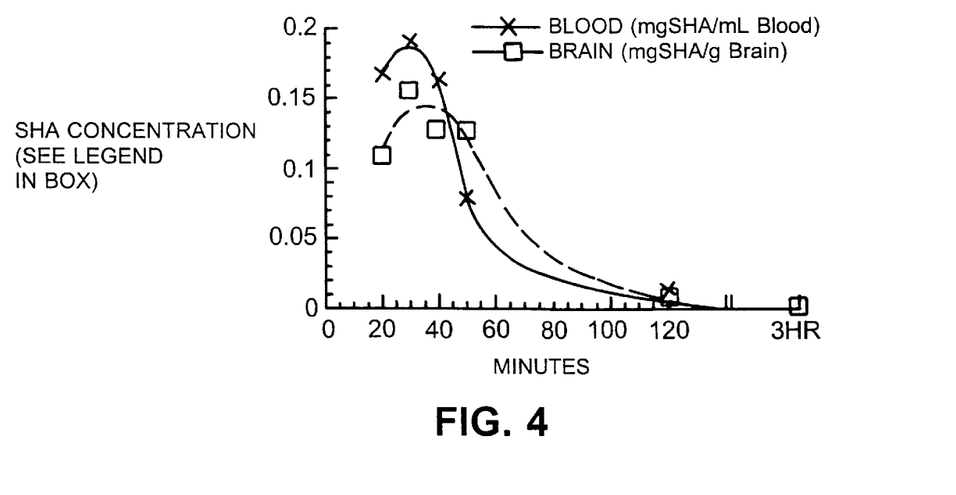
FIG. 4 is a line graph depicting the pharmacokinetics of salicylhydroxamic acid (SHA).

SHA (400 mg/kg) was injected intraperitoneally (i.p.) into Sprague-Dawley rats. At fixed time intervals after injection, blood samples were collected, and perfused brain was removed and homogenized. Acidified blood and brain samples were extracted in ethyl acetate. SHA was quantitated by reverse phase HPLC at 310 nm, and compared to known amounts of standards that had been added to blood or brain tissue as shown in FIG. 4.

Three important points can be raised from this study: (1) SHA is able to cross the blood-brain barrier quite effectively in normal brain; (2) the concentration of SHA in blood and brain during the first 2 hours after the injection exceeds the complement C3 inhibitory $IC_{50}$ value of SHA (8.3 $\mu$M, or equivalent to 0.0013 mg SHA/g brain),therefore, SHA at 400 mg/kg i.p. should be sufficient to suppress complement activation for approximately 2 hours after administration of each dose; and (3) the peak concentration of SHA in both blood and brain appears to be about 30 minutes after drug administration. The time of SHA injection after the onset of ischemia or reperfusion can be systematically varied to determine other ranges in which therapeutic intervention is available using this drug.

Attenuation of Cerebral Ischemia and Reperfusion Injury with SHA

Figure 5:
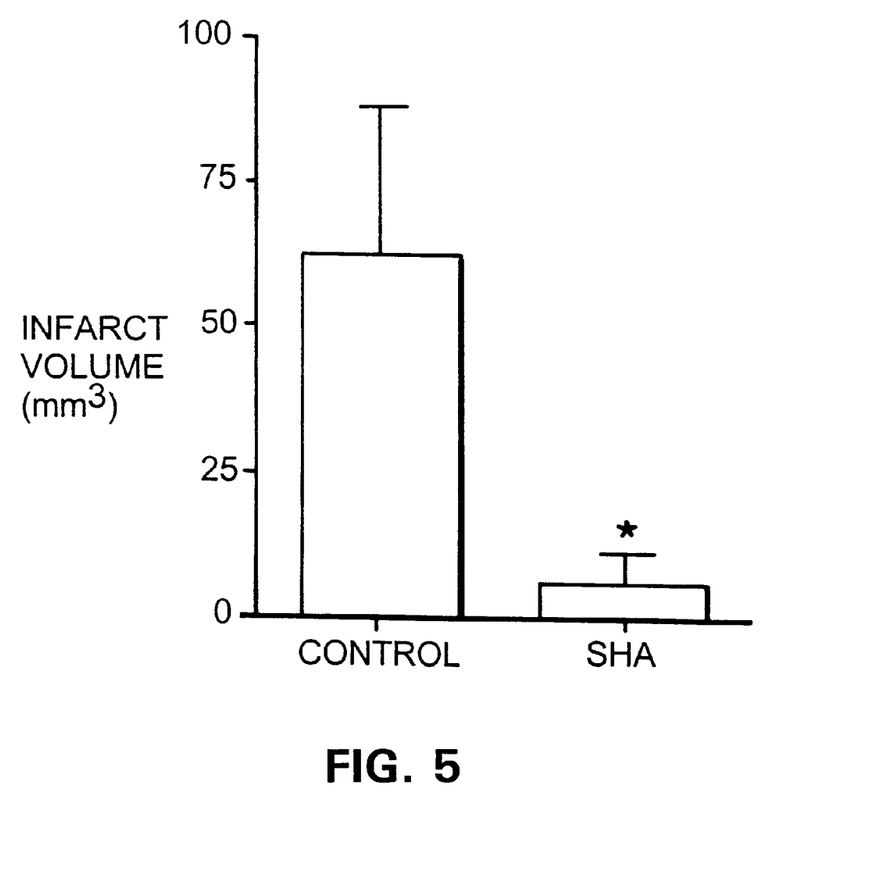
FIG. 5 is a graph depicting the infarct volume of C57BL/6 mice subjected to middle cerebral artery occlusion and treated with saline (Control, n=3) or SHA (SHA, n=3).

SHA was tested for its ability to prevent cytotoxic damage by using the middle cerebral artery (MCA) occlusion stroke model (Longa et al., supra). Briefly, this system involves anesthetizing mice with isoflurane and then maintaining the body temperature of the mice at 36±1° C. A 6.0 monofilament nylon suture with silicone-coated tip was then advanced into the internal carotid artery about 9 mm via the external carotid artery. Immediately after the filament was secured, SHA (400 mg/kg i.p.) or vehicle (normal saline) was injected. At 1.5 hours after the first injection, a second i.p. injection was given to the animal. 2 hours later the animals were re-anesthetized and the filament was removed to allow reperfusion. Cerebral blood flow, blood pressure, blood gases, pH, and serum glucose were monitored in these studies. At 24 hours the animals were sacrificed, brains removed and 1 mm thick brain section are cut on a vibratome. The brain slices were stained with 2% triphenyltetrazolium choloride. The infarct volume was obtained as described in Swanson et al., supra with results being (mean+SEM, n=3 in each group) 62.6±34.2 $mm^3$ in the vehicle-treated group versus 6.1±6.0 $mm^3$ in the SHA-treated group. As shown in FIG. 5, the normal saline control group sustained much larger infarct volume that that of the SHA treated group.

What is claimed is:

1. A method of treating cytotoxic damage mediated through glutamate receptors and associated with non-thrombotic conditions in a subject, comprising administering to said subject a substance which is a complement inhibitor, a free radical scavenger, or both, wherein the substance is salicylhydroxamic acid (SHA) or acetohydroxamic acid (AHA), thereby ameliorating cytotoxic damage associated with non-thrombotic conditions in said subject.

2. The method of claim 1, wherein said subject is a human.

3. The method of claim 1, wherein said non-thrombotic condition is Huntington's disease.

4. The method of claim 1, wherein said non-thrombotic disorder is hypoglycemia.

5. The method of claim 1, wherein said non-thrombotic condition is a convulsive disorder.

6. The method of claim 1, wherein said non-thrombotic condition is neuropathic pain.

7. The method of claim 1, wherein said non-thrombotic condition is glaucoma.

8. The method of claim 1, wherein said non-thrombotic condition is selected from the group consisting of drug addiction, drug dependence, drug withdrawal, and drug tolerance.

9. The method of claim 1, wherein said substance can cross the blood-brain barrier.

10. The method of claim 1, wherein said substance is administered in a pharmaceutically acceptable formulation.

11. The method of claim 1, wherein said substance is administered intraperitoneally.

12. The method of claim 1, wherein said substance is administered orally, intravascularly, subcutaneously, intradermally, intramuscularly, intranasally, intracerebralventricularly (ICV), or intrathecally.

13. The method of claim 1, wherein said substance is administered at a level of approximately 40–4,000 mg/Kg.

14. The method of claim 1, wherein said substance is administered at a level of approximately 200–2,000 mg/Kg.

15. The method of claim 1, wherein said substance is administered at a level of approximately 400–1,000 mg/Kg.

16. The method of claim 1, wherein said non-thrombotic disoder is AIDS dementia complex.

17. The method of claim 1, wherein said non-thrombotic disorder is neuropathic pain syndromes.

18. The method of claim 1, wherein said non-thrombotic disorder is Olivopontocerebellar atrophy.

19. The method of claim 1, wherein said non-thrombotic disorder is Parkinsonism.

20. The method of claim 1, wherein said non-thrombotic disorder is amyotrophic lateral schlerosis.

21. The method of claim 1, wherein said non-thrombotic disorder is mitochondrial abnormalities.

22. The method of claim 1, wherein said non-thrombotic disorder is MELAS syndrome.

23. The method of claim 1, wherein said non-thrombotic disorder is Alzheimer's disease.

24. The method of claim 1, wherein said non-thrombotic disorder is Tourette's syndrome.

25. The method of claim 1, wherein said non-thrombotic disorder is epilepsy.

26. A method of treating cytotoxic damage in a subject, comprising administering a thrombolytic agent to said subject and administering to said subject a substance which is a complement inhibitor, a free radical scavenger, or both, wherein said substance is salicylhydroxamic acid (SHA) or acetohydroxamic acid (AHA), thereby treating cytotoxic damage in said subject.

27. The method of claim 26, wherein said thrombolytic agent is a fibrinolytic agent.

28. The method of claim 27, wherein said fibrinolytic agent is streptokinase.

29. The method of claim 27, wherein said fibrinolytic agent is urokinase.

30. The method of claim 26, wherein said fibrinolytic agent is selected from the group consisting of tissue-plasminogen activator and Desmodus salivary plasminogen activator (dsPA).

31. The method of claim 30, wherein said tissue-plasminogen activator (t-PA) is a recombinantly produced tissue-plasminogen activator (t-PA).

32. The method of claim 26, wherein said subject is suffering from stroke.

33. The method of claim 26, wherein said subject is suffering from ischemia.

34. The method of claim 33, wherein said subject is suffering from cerebral ischemia.

35. The method of claim 34, wherein said subject is suffering from focal cerebral ischemia.

36. The method of claim 34, wherein said subject is suffering from global cerebral ischemia.

37. The method of claim 34, wherein said subject is suffering from hypoxia ischemia.

38. The method of claim 26, wherein said subject is a human.

39. The method of claim 26, wherein said subject is suffering from neuropathic pain.

40. The method of claim 26, wherein said subject is suffering from glaucoma.

41. The method of claim 26, wherein said subject is suffering from a condition selected from the group consisting of drug addiction, drug dependence, drug withdrawal, and drug tolerance.

42. The method of claim 26, wherein said substance can cross the blood-brain barrier.

43. The method of claim 26, wherein said substance is administered in a pharmaceutically acceptable formulation.

44. The method of claim 26, wherein said substance is administered intraperitoneally.

45. The method of claim 26, wherein said substance is administered orally, intravascularly, subcutaneously, intradermally, intramuscularly, intranasally, intracerebralventricularly (ICV), or intrathecally.

46. The method of claim 26, wherein said substance is administered at a level of approximately 40–4,000 mg/Kg.

47. The method of claim 26, wherein said substance is administered at a level of approximately 200–2,000 mg/Kg.

48. The method of claim 26, wherein said substance is administered at a level of approximately 400–1,000 mg/Kg.

49. The method of claim 26, wherein said cytotoxic damage is mediated through glutamate receptors.

50. A method of treating plasminogen activator induced cytotoxic damage in a subject suffering from stroke, comprising administering to said subject a substance which is a complement inhibitor, a free radical scavenger, or both, wherein said substance is salicylhydroxamic acid (SHA) or acetohydroxamic acid (AHA) and is able to cross the blood-brain barrier, thereby treating plasminogen activator induced cytotoxic damage in said subject.

51. The method of claim 50, wherein the plasminogen activator induced cytotoxic damage is tissue plasminogen activator (tPA) induced cytotoxic damage.

52. The method of claim 50, wherein the plasminogen activator induced cytotoxic damage is Desmodus salivary plasminogen activator (dsPA) induced cytotoxic damage.

53. A method of treating plasminogen activator induced cytotoxic damage in a subject suffering from cerebral ischemia, comprising administering to said subject a substance which is a complement inhibitor, a free radical scavenger, or both, wherein said substance is salicylhydroxamic acid (SHA) or acetohydroxamic acid (AHA) and is able to cross the blood-brain barrier, thereby treating plasminogen activator induced cytotoxic damage in said subject.

54. The method of claim 53, wherein the plasminogen activator induced cytotoxic damage is tissue plasminogen activator (tPA) induced cytotoxic damage.

55. The method of claim 53, wherein the plasminogen activator induced cytotoxic damage is Desmodus salivary plasminogen activator (dsPA) induced cytotoxic damage.

* * * * *

UNITED STATES PATENT AND TRADEMARK OFFICE
CERTIFICATE OF CORRECTION

PATENT NO.    : 6,503,947 B1
DATED         : January 7, 2003
INVENTOR(S)   : Stuart Lipton et al.

It is certified that error appears in the above-identified patent and that said Letters Patent is hereby corrected as shown below:

<u>Title page,</u>
Item [56], OTHER PUBLICATIONS,
Reference "Meldrum et al.," replace "Science" with -- Sciences --.
Reference "Buchan et al.," replace "Modle" with -- Model --.
Reference "Taparelli, C.," replace "Mlecular" with -- Molecular --.
Item [57], ABSTRACT,
Line 2, replace "comprising" with -- which includes --.
Line 8, replace "subject, comprise" with -- subject can include --.

Signed and Sealed this

Twenty-second Day of July, 2003

JAMES E. ROGAN
*Director of the United States Patent and Trademark Office*

UNITED STATES PATENT AND TRADEMARK OFFICE
CERTIFICATE OF CORRECTION

PATENT NO. : 6,503,947 B1
DATED : January 7, 2003
INVENTOR(S) : Stuart Lipton et al.

It is certified that error appears in the above-identified patent and that said Letters Patent is hereby corrected as shown below:

<u>Column 1,</u>
Line 6, please insert the following paragraph
-- FEDERALLY SPONSORED RESEARCH OR DEVELOPMENT
The U.S. Government may have certain rights in this invention pursuant to Grant No. NIH/NICHD P01 HD29587 awarded by the National Institutes of Health. --

Signed and Sealed this

Thirteenth Day of April, 2004

JON W. DUDAS
*Acting Director of the United States Patent and Trademark Office*